US006709392B1

(12) United States Patent
Salgo et al.

(10) Patent No.: US 6,709,392 B1
(45) Date of Patent: *Mar. 23, 2004

(54) IMAGING ULTRASOUND TRANSDUCER TEMPERATURE CONTROL SYSTEM AND METHOD USING FEEDBACK

(75) Inventors: Ivan Salgo, Andover, MA (US); Michael Peszynski, Newburyport, MA (US); David Miller, Woburn, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 10/268,261

(22) Filed: Oct. 10, 2002

(51) Int. Cl.[7] ................................................ A61B 8/00
(52) U.S. Cl. ........................... 600/439; 601/2; 600/437
(58) Field of Search ............................... 600/437, 439, 600/438, 462, 466, 467, 471; 601/1, 2, 3, 4; 607/101, 102; 606/1

(56) References Cited

U.S. PATENT DOCUMENTS

| 4,638,436 A | * | 1/1987 | Badger et al. .............. 607/102 |
| 5,213,103 A | | 5/1993 | Martin et al. .......... 128/660.07 |
| 5,472,405 A | * | 12/1995 | Buchholtz et al. ............. 601/2 |
| 5,555,887 A | | 9/1996 | Fraser et al. ........... 128/663.01 |
| 5,560,362 A | | 10/1996 | Sliwa, Jr. et al. ....... 128/660.03 |
| 5,721,463 A | | 2/1998 | Snyder ....................... 310/334 |
| 6,001,069 A | * | 12/1999 | Tachibana et al. .............. 601/2 |
| 6,210,356 B1 | | 4/2001 | Anderson et al. ............. 604/22 |
| 6,427,089 B1 | * | 7/2002 | Knowlton ................... 607/101 |
| 6,500,121 B1 | * | 12/2002 | Slayton et al. .............. 600/439 |

* cited by examiner

Primary Examiner—George Manuel
Assistant Examiner—Ruby Jain
(74) Attorney, Agent, or Firm—John Vodopia

(57) ABSTRACT

A system and method for controlling the heat of an ultrasonic transducer is disclosed. In the presently preferred embodiments, the system and method controls the temperature of the transducer by changing operating system parameters based on feedback from temperature sensing elements placed in the transducer. The chosen mutable system parameters may be preset by the construction of the ultrasonic system, under the control of the ultrasonic system user, or a combination of the two. In one exemplary embodiment, a different mutable system parameter is altered based on which imaging mode the system is using. In two other exemplary embodiments, the one or more mutable system parameters are altered by an amount proportionate to the difference between the current temperature and a preferred operating temperature. In yet another exemplary embodiment, the system switches to a lower power imaging mode when the temperature feedback indicates a threshold temperature has been reached.

21 Claims, 8 Drawing Sheets

IMAGING ULTRASOUND TRANSDUCER TEMPERATURE CONTROL SYSTEM AND METHOD USING FEEDBACK

BACKGROUND OF THE INVENTION

1. Field of the Invention

The invention relates generally to the field of imaging ultrasonic medical transducer assemblies, and, specifically, to an apparatus and method for cooling the transducer.

2. Description of the Related Art

Ultrasonic medical transducers are used to observe the internal organs of a patient. The ultrasonic range is described essentially by its lower limit: 20kHz, roughly the highest frequency a human can hear. The medical transducers emit ultrasonic pulses which echo (i.e., reflect), refract, or are absorbed by structures in the body. The reflected echoes are received by the transducer and these received signals are translated into images. Such translation is possible because the reflections from the internal organs vary in intensity according to the "acoustic impedance" between adjacent structures. The acoustic impedance of a tissue is related to its density; the greater the difference in acoustic impedance between two adjacent tissues the more reflective their boundary will be.

The frequency of the ultrasonic beams has an effect on both the image resolution and the penetration ability of the ultrasonic device. Higher frequency ultrasound waves have a longer near field (i.e., the region in the sound beam's path where the beam diameter decreases as the distance from the transducer increases) and less divergence in the far field (i.e., the region in the sound beam's path where the beam diameter increases as the distance from the transducer increases): higher frequency ultrasonic waves thus permit greater resolution of small structures. However, high frequency ultrasonic waves have less penetrating ability because their energy is absorbed and scattered by soft tissues. On the other hand, lower frequency ultrasonic waves have a greater depth of penetration, but the received images are much less well defined. The conventional frequency range for imaging human internal organs (using sound waves) is typically from about 3 MHz to about 5 MHz.

Two types of resolution generally apply to ultrasound imaging transducers: lateral resolution and axial resolution. Lateral resolution is the ability to resolve objects side by side and, as discussed above, is proportionally affected by the frequency (the higher the frequency, the higher the lateral resolution). Higher frequency transducers are used for infants and children because there is less need for deep penetration and the smaller structures can be viewed with greater lateral resolution. Lower frequencies are used for adults where the internal structures are larger and there is a greater need for depth penetration. Of course, when determining the appropriate frequency to be used, the structure, tissue, or organ to be viewed (and the exact purpose of the imaging) can matter more than the age of the subject. For example, diagnostic breast imaging on an adult may require a frequency of about 7 MHz or higher.

Axial resolution is the ability to resolve objects that lie one above the other. Because this is related to depth penetration, axial resolution is inversely proportional to the frequency of the transducer (depending on the size of the patient). In large patients, higher frequency beams are rapidly absorbed by the objects closest to the transducer, thus reducing depth penetration and axial resolution.

The focusing of an ultrasonic transducer can be implemented in one of two ways: mechanical or electronic. Mechanical focusing consists of placing an acoustic lens on the surface of the transducer or using a transducer with a concave face. One or several piezoelectric elements are used. In order to create a sweeping beam for 2D imaging, a single element may be oscillated back and forth, several elements may be rotated, or a single element may be used with a set of acoustic mirrors. This last transducer type (with the acoustic mirrors) is sometimes called the "wobbler" because of the vibration created as the mirrors rotate or oscillate inside the housing.

Electronic focusing uses a process called phased array, where multiple piezoelectric elements in an array are stimulated (or "fired") sequentially in order to form and focus the beam. In an annular array, circular or ringlike elements and/or arrays are used. In a linear array, a row of elements is used to form and focus the beam. A transducer contains an array of transmitting elements and a similar array of receiving elements. An example of how a linear array forms and focuses a sound beam is shown in FIG. 1. In order to focus at point X, the outer elements 101 and 107 fire first, then elements 102 and 106, then elements 103 and 105, and finally element 104. As shown in FIG. 1, the resulting wavefronts combine to form a semicircular ultrasonic pulse whose focal point is X. By varying the sequential pattern of firing, the distance of focal point X from the transducer can be changed. Furthermore, varying the sequential pattern of firing can also be used to steer the beam. Steering is used to move focal point X left and right in FIG. 1. By rapidly steering a series of beams from left to right, a 2D cross-sectional image may be formed.

In 2D mode, one sweep from left to right is a frame, and the number of sweeps in a second is the frame rate (or fps—frames per second). Conventional frame rates ranges from about 12 fps to about 30 fps. The number of beams formed over time is the Pulse Repetition Frequency (PRF), measured in pulses per second. The range of PRFs for most commercial echocardiographs is between about 200 and about 5000 pulses per second. PRF varies with the type of imaging being performed. Most of the time spent in each second is used waiting for the echoes to return to the receiving elements in the transducer. In other words, after a beam is formed, the transmitting elements lie dormant while the beam travels to the various objects and then some of that sound energy returns (as echoes) to the transducer's receiving elements. The amount of time that the transmitting elements are transmitting sound energy is called the duty factor. Most transducers are acting as a receiver about 99% of the time, in which case the duty factor is 1 (%).

Aperture is the size of the active transmitting and receiving portion of a transducer array. Aperture is measured in square centimeters and is a function of the number of transducer elements used simultaneously to form an image. A common measurement of aperture size is F-number or F#, which is defined as the ratio of depth to aperture. These values are related to the lateral resolution (LR) by the following function:

$$LR = \lambda * F\# = \lambda * \frac{D}{A}$$

As can be seen from the above equation, for a fixed frequency, the aperture size must increase as the scanning depth increases in order to maintain uniform lateral resolution throughout the image. Many ultrasonic systems select a transmit aperture based on the scan depth setting and continuously vary the reception aperture. It is desirable to achieve low F#s, which, because the scanning depth is limited by the position of the desired subject, is identical to seeking larger aperture sizes. It is also desirable to seek small wavelengths, which is equivalent to seeking higher frequencies.

There are a number of modes in which an ultrasonic transducer operates. The basic modes are A Mode, B Mode, M Mode, and 2D Mode. The A Mode is amplitude mode, where signals are displayed as spikes that are dependent on the amplitude of the returning sound energy. The B Mode is brightness mode, where the signals are displayed as various points whose brightness depends on the amplitude of the returning sound energy. The M Mode is motion mode, where B Mode is applied and a strip chart recorder allows visualization of the structures as a function of depth and time. The 2D Mode is two-dimensional (imaging) mode, where B Mode is spatially applied by sweeping the beam (as described above) so that structures are seen as a function of depth and width.

2D Mode refers to the most basic, fundamental imaging mode. There are other imaging modes, which also image in two dimensions (in three dimensions in some new technologies), but these are referred to by their own names, usually based on the type of technology/methodology used to produce the image. Some of these other imaging modes will be described below. When the term 2D Mode is used, it only refers to the basic spatially oriented B Mode, and not all two dimensional imaging modes.

There have been various solutions to the problem of higher frequency-greater resolution-less depth penetration and lower frequency-lower resolution-greater depth penetration. One solution is harmonic imaging. With conventional imaging, the ultrasound system transmits and receives a sound pulse of a specific frequency (the "fundamental" frequency). As discussed above, parts of the sound pulse are reflected back to the transducer, where the reflected sound at the fundamental frequency is processed. In harmonic imaging, the transducer does not listen for the fundamental frequency, but for other frequencies—most notably, the "harmonic" frequency, which is twice the fundamental frequency (this is sometimes referred to as the "first harmonic"). To be more technically accurate, the transducer receives a signal comprised of a number of frequencies, including the fundamental and harmonic, and separates out the signal at the harmonic frequency (the "harmonic" for short). Once separated out, the harmonic is processed to produce an image.

Harmonics are generated by the object being imaged, either with or without the assistance of human intervention. When assisted, harmonics are generated by ultrasound "contrast agents" which are injected into the patient's body. These contrast agents generally contain very small bubbles which generate two kinds of echoes when struck by a pulse. First, the conventional echo is bounced back based on the fundamental frequency. But then the bubble vibrates (in response to the pulse), thereby generating a harmonic signal. Because these contrast agents are formed for the purpose of creating harmonic echoes (rather like a bell when struck by a clapper), very strong echoes are generated at the harmonic frequency, thereby producing excellent high contrast images.

When not relying on contrast agents, harmonic imaging uses the harmonics that are generated by the tissue of the body itself (having been "rung" by the ultrasonic pulse). Obviously, these harmonics do not generate as clear a picture as the harmonics from contrast agents. The ability to create harmonics in tissue varies depending on the tissue's location in the ultrasound beam's field of view. The most pronounced imaging effect is from harmonics located at and around the focal point of the ultrasonic beam (i.e., mid-field). No harmonics are generated by tissue in the near field, and the harmonics generated in the far field attenuate quickly after being produced.

Harmonic imaging has a number of advantages. The beam formed at the harmonic frequency is narrower and has lower side-lobes, thereby significantly improving grayscale contrast resolution. Furthermore, since the harmonics are generated inside the body, they only pass through the fat layer once, rather than twice.

Some other modes of imaging are dependent on the Doppler effect, the phenomena whereby the frequency of sound from an approaching object has a higher frequency and, conversely, sound from a receding object has a lower frequency. In ultrasonic systems, this effect is used to determine the velocity and direction of blood flow in a subject. Doppler techniques can also be used with ultrasonic transducers which operate in continuous wave mode (i.e., part of the transducer array transmits while another part simultaneously receives).

Pulsed wave Doppler effect techniques have proven to be very accurate in blood flow studies. However, if the velocity of the blood flow being measured exceeds the Nyquist Limit (half the PRF), the ultrasonic readings become inaccurate. Most Doppler techniques try to achieve a high a PRF as possible in order to avoid this effect. One type of imaging, Color Flow Imaging or CFI, uses this effect (called "aliasing") to detect flow disturbances, e.g., transitions from laminar to turbulent flow. In CFI, multiple sample volumes are detected and displayed utilizing color mapping for direction and velocity flow data. Common mapping formats are BART (Blue Away, Red Towards), RABT (Red Away, Blue Towards), or enhanced/variance flow maps where color saturations indicate turbulence/acceleration and color intensities indicate higher velocities. Some maps use a third color, green, to indicate accelerating velocities and turbulence.

It is desirable for the ultrasonic system to operate at the highest frequency (for the reasons discussed above) and at the maximum acoustic intensity. Maximizing the acoustic intensity increases imaging performance by increasing the depth penetration and maximizing the signal to noise ratio (SNR). However, higher frequencies and greater acoustic intensities cause the ultrasonic transducer to heat up, and there are regulatory limits (and practical limits) on the surface temperature of an ultrasonic probe when interacting with a subject. Specifically, the upper temperature limit on the patient contact surface of an ultrasonic transducer is generally considered to be about 41° C. or about 16° C. above ambient temperature.

The heat of the transducer surface is generated both by the electroacoustic energy conversion process taking place in the transducer's piezoelements and by the acoustic energy passing through and/or into adjacent transducer materials (and the patient herself). Different methods and systems have been developed to deal with the heating problem and they can be broken into two types: active and passive. Passive solutions use passive cooling mechanisms, i.e., spreading out the dissipated heat to as large an external transducer surface area as possible. Typically, the heat generated by the transducer array is absorbed by solid thermal conductors, and then this captured heat is moved by thermal convection into the transducer's external case, where it can dissipate in the atmosphere. Ideally, the external heat-convecting surface area would consist of the transducer's entire external surface area.

One example of a passive heat dissipation system is U.S. Pat. No. 5,213,103 ('103 patent), which is hereby incorporated by reference in its entirety. FIG. 2 shows the outside of the transducer in the '103 patent. A heat sink device (internal to the transducer, thus not shown) placed inside the transducer 10 behind the piezoelectric elements in the face 14 (i.e., the patient contact surface) on the head 12 of transducer 10. The heat sink extends the entire length of the transducer and conducts heat away from face 14, through head 12, to the sides of handle 16 and power cable 18. Heat conductive epoxy is used both to attach the heat sink to the transducer housing and to conduct the heat from the heat sink to the transducer housing.

Another example of a passive heat dissipation system is U.S. Pat. No. 5,555,887 ('887 patent), which is hereby incorporated by reference in its entirety. The '887 patent applies heat dissipation to an endoscopic ultrasound transducer by embedding aluminum foil in acoustic lens material in front of the transducer array. Heat is conducted by the aluminum foil to a heat sink positioned at a distance from the patient contacting surface of the probe. U.S. Pat. No. 5,721,463 ('463 patent), which is hereby incorporated by reference in its entirety, describes a passive heat dissipation system which uses a bundle of coaxial cables to vent heat away from the face of the probe.

These passive heat sinks are effective, but they also add to the transducer's overall thermal dissipation resistance. The fundamental limitation is that, for most transducers, even if heat is spread uniformly on the external case surfaces, it only takes a few watts of transducer driving power to cause the average transducer surface temperature to become unacceptable either with respect to the patient or the sonographer. In these cases, and particularly for small transducers having small surface areas, one may find that one is unable to operate at the allowable acoustic intensity limit because of excessive temperatures.

Active solutions, on the other hand, use active cooling means, such as circulating coolant systems. One example, U.S. Pat. No. 5,560,362 ('362 patent), which is hereby incorporated by reference in its entirety, describes a heat dissipation system in which a pumping or pressurization means actively circulates a gaseous or liquid coolant in a cable, part of which is nearby the transducer array. The system can be a single pass, multipass, or closed loop circulating system, and the coolant may pass through a heat exchanger, a heat pipe, a thermoelectric cooler, an evaporator/condenser system, and/or a phase change material.

An ultrasonic transducer cooling system which uses feedback control is shown in U.S. Pat. No. 6,210,356 ('356 patent), which is hereby incorporated by reference in its entirety. The '356 patent is directed to a catheter which provides ultrasonic energy (and perhaps medicine) as a therapeutic treatment to a site inside a patient's body. Thus, no imaging or sensing is being performed by the ultrasonic transducer in the '356 patent. Temperature sensors are positioned in the surface coating of the catheter next to the ultrasound transducer in order to provide a measure of the temperature on the exterior surface of the catheter. This measure is used as a feedback control signal for the power circuits of the ultrasonic transducer. After the user sets a predetermined temperature, the power circuits decrease or increase power in the same proportion as the measured temperature is above or below the predetermined temperature.

The device described in the '356 patent also includes safety control logic which detects when the temperature at a temperature sensor has exceeded a safety threshold. When this occurs, the power circuits stop providing power to the ultrasonic transducer. However, such a feedback control system can be inappropriate for ultrasonic imaging/measuring applications.

Although abruptly turning off the power during a therapeutic ultrasonic session may not be damaging, abruptly turning off the power during an imaging/measuring session can be potentially dangerous (e.g., a sudden blackout during a surgical procedure). Even when not dangerous, turning off the image makes the diagnosis and analysis of image data difficult. Thus, there is a need for a system and method for reducing the temperature of the ultrasonic transducer in general, and the patient contacting surface in specific, which does not merely turn the transducer off. Furthermore, there is a need for a system and method which may work either as a replacement for the conventional active or passive heat dissipation systems or as an adjunct to them.

SUMMARY OF THE INVENTION

One object of the present invention is to provide a system and method for reducing the temperature of an imaging ultrasonic transducer in general, and the patient contacting surface in specific, without merely turning the transducer off.

Another object of the present invention is to provide a system and method for reducing the temperature of an imaging ultrasonic transducer which may work either as a replacement for the conventional active or passive heat dissipation systems or as an adjunct to them.

Yet another object of the present invention is to provide a system and method by which an operator of an imaging ultrasonic transducer system may control the manner in which the ultrasonic transducer system changes parameters in order to cool the ultrasonic transducer.

These and other objects are achieved by the present invention in which a system and method control the temperature of an imaging ultrasonic transducer by changing mutable system parameters based on feedback from temperature sensing elements placed in the transducer. The chosen mutable system parameters may be preset by the construction of the ultrasonic system, under the control of the ultrasonic system user, or a combination of the two.

In one exemplary embodiment, a different mutable system parameter is altered based on which imaging mode the system is using. In two other exemplary embodiments, the one or more mutable system parameters are altered by an amount proportionate to the difference between the current temperature and a preferred operating temperature. In another exemplary embodiment, the system switches to a lower power imaging mode when the temperature feedback indicates a threshold temperature has been reached. In still another exemplary embodiment, the steps from other exemplary embodiments are combined.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

The present invention is directed to a novel system and method of controlling the radiant heat from the patient contact surface of an ultrasonic transducer. Although the details of implementation may be different in different embodiments, the present invention is not limited to any particular type of ultrasonic transducer or any particular mode of imaging and/or data analysis. The presently preferred embodiments of the present invention control the temperature of the transducer face by changing operating system parameters based on feedback from temperature sensing elements placed in the transducer. Which operating parameters are changed and the manner in which the chosen parameters change depends upon the imaging mode, the type of heat dissipation system being used (if any), the particular ultrasonic system, etc. In addition, these choices may be preset by the construction of the ultrasonic system, under the control of the ultrasonic system user, or a combination of the two.

Figure 1:
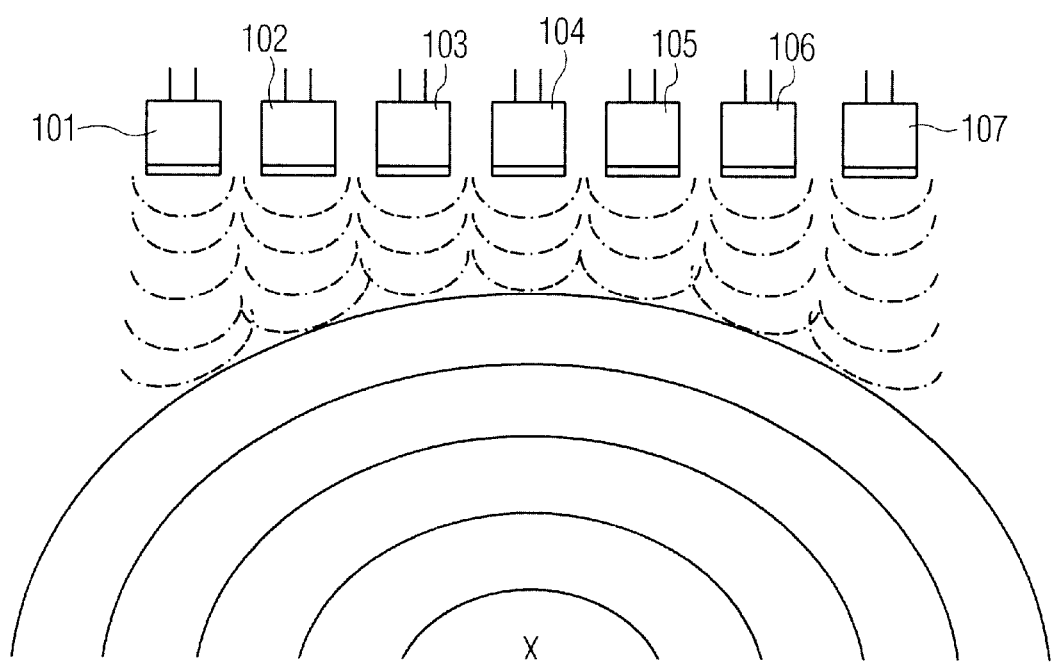
FIG. 1 shows how typical ultrasonic beam is formed by a linear array of piezoelectric elements.
Figure 2:
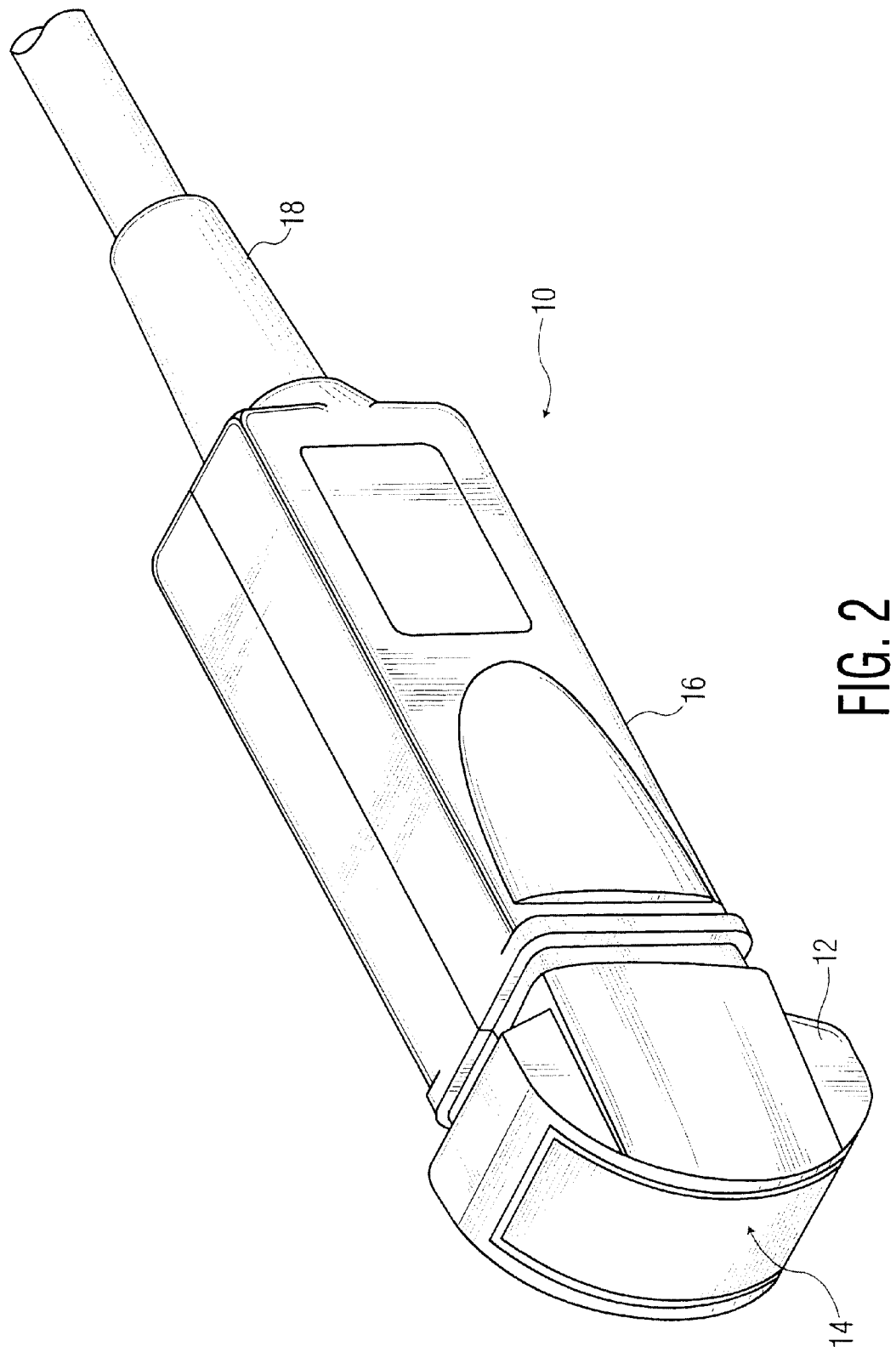
FIG. 2 shows a prior art ultrasonic transducer probe.
Figure 3:
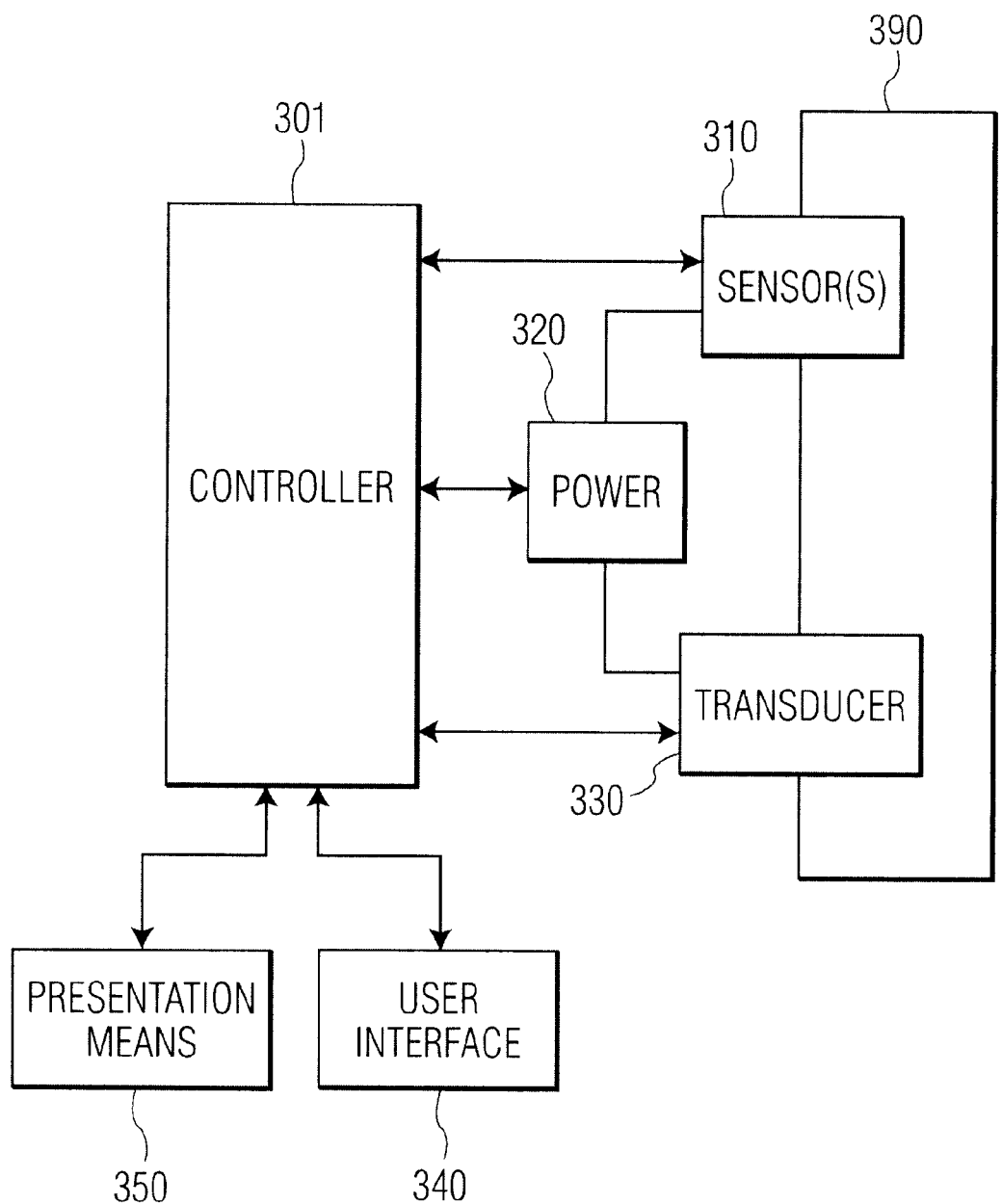
FIG. 3 is a block diagram showing the functional modules of an ultrasonic transducer system according to a preferred embodiment of the present invention.

A block diagram of the functional modules in a preferred embodiment of the present invention is shown in FIG. 3. Each of the functional modules should be understood as an abstraction of the function or combination of functions named, and each can be combined or further divided as necessary for implementing a particular embodiment. These functions may be implemented in software, hardware, or a combination of the two.

In FIG. 3, a controller 301, which may take the form of a microprocessor, controls the overall functioning of the ultrasonic device. Controller 301 receives measurement signals from temperature sensor(s) 310. Possible temperature sensors include any known conventional temperature sensor, such as, for example, thermistors, thermocouples, resistance temperature detectors (RTDs), and fiber optic temperature sensors which use thermalchromic liquid crystals. There may be one or more temperature sensor(s) 310, and their appropriate placement within the ultrasonic system will depend on the use and type of system, as would be known to one skilled in the art. In the preferred embodiments, the appropriate placement of the temperature sensor(s) 310 is the most suitable location to ascertain the surface temperature of the patient contacting surface 390 of the ultrasonic transducer.

Power supply 320, under control of controller 301, supplies power to the various components of the ultrasonic system. For example, controller 320 controls the amount of power sent to the ultrasonic transducer 330. Ultrasonic transducer 330 is also under the control of controller 301. The present invention is not limited to any particular type of imaging ultrasonic system, nor to any particular imaging or non-imaging mode. User interface 340 allows the user to monitor the condition of, and/or to interact with, the ultrasonic system; it may comprise a keyboard (and mouse), a microphone (and voice recognition software), a handheld input device, or any other form of input device compatible with the present invention. Presentation means 350 is for presenting system parameters, and may or may not be used to see the results of the ultrasonic testing being performed. Presentation means 350 may comprise a display monitor, a speaker (with either voice synthesis or pre-recorded speech), or any other means of presenting the status of system parameters and/or allowing the user to interact with the ultrasonic system.

Although not necessary, an ultrasonic system according to the present invention may also comprise a passive or active heat dissipation system. In some embodiments of the present invention, the present invention itself acts as the sole heat dissipation system for the ultrasonic transducer.

Figure 4:
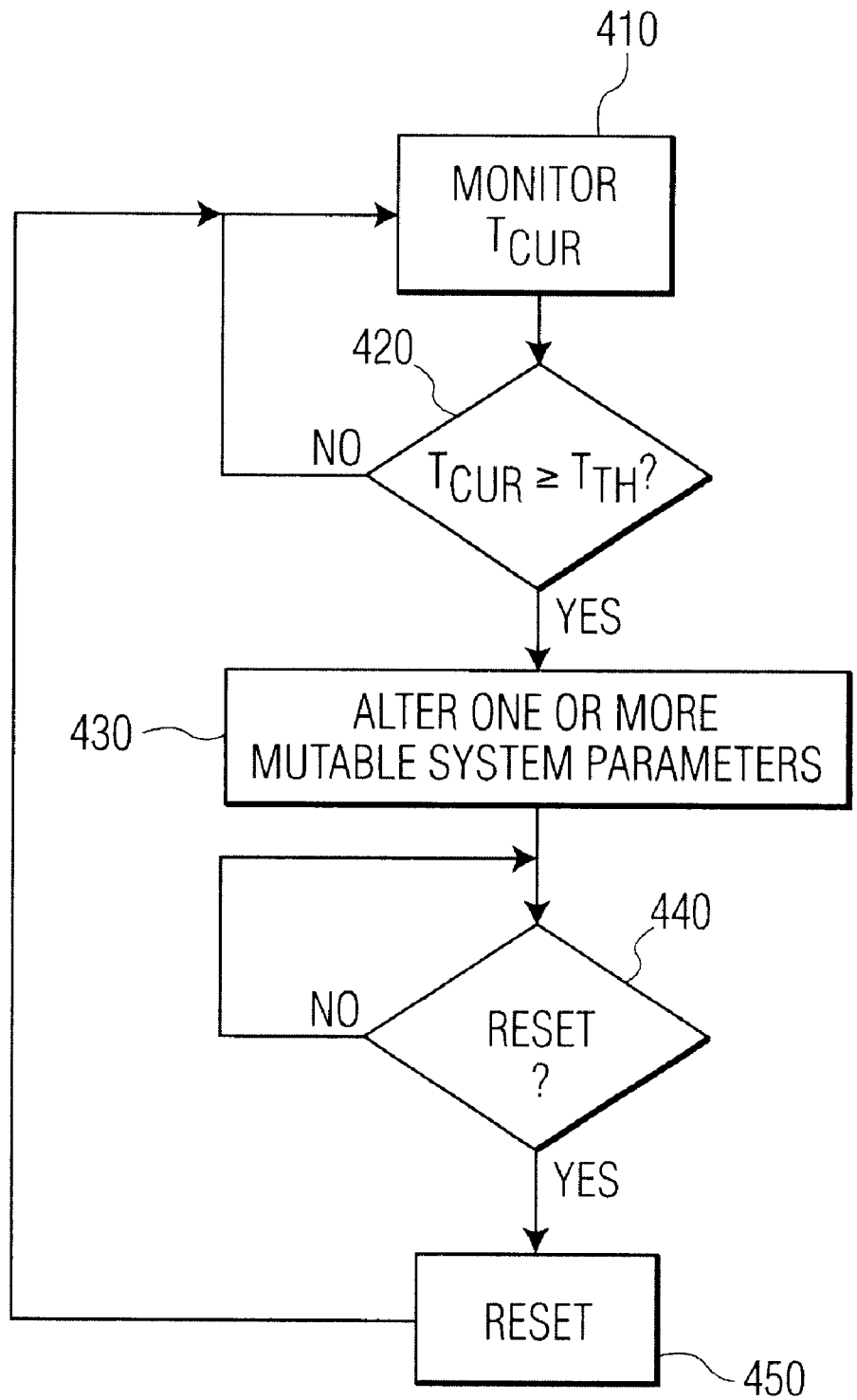
FIG. 4 is a flowchart of a temperature cooling method according to a preferred embodiment of the present invention.

The imaging ultrasonic system temperature control method according to the present invention is shown in its broadest aspect by FIG. 4. In step 410, the current temperature $T_{cur}$ of the patient contacting surface 390 of the ultrasonic transducer 330 is monitored by controller 301. In step 420, it is determined whether the current temperature $T_{cur}$ has exceeded a threshold temperature $T_{th}$. The threshold temperature $T_{th}$ may be any temperature under (or equal to) the critical temperature $T_c$ at which discomfort or damage may occur to the patient. Obviously, in embodiments where $T_{th}$ equals the critical temperature $T_c$, the assumption is that the subsequent steps will reduce the temperature so quickly that no discomfort will come to the patient. If the current temperature $T_{cur}$ is below the threshold temperature $T_{th}$ in step 420, the system returns to monitoring step 410.

On the other hand, if the current temperature $T_{cur}$ is greater than, or equal to, the threshold temperature $T_{th}$ in step 420, the system changes one or more system parameters (called "mutable system parameters") in order to reduce the temperature in step 430. This description refers to the mutable system parameters as being "changed" rather than merely reduced (or increased) to indicate that the present invention applies to a wide variety of "changes" that may be made to the system parameters in addition to a simple reduction.

In one preferred embodiment, the one or more mutable system parameters to be changed are predetermined, i.e., they are hardwired in the apparatus or preprogrammed in the software. In another preferred embodiment, the operator selects the mutable system parameter(s) as well as the type and amount of change to the mutable system parameter(s).

After the one or more mutable system parameters have been changed in step 430, the system determines whether it should be reset to "nominal" operating conditions in step 440. If so, the system resets in step 450; if not, the system continues checking whether it should reset. In a preferred embodiment, the nominal operating conditions are how the mutable system parameters were set before step 430. In some embodiments, the user may reset the system him- or herself. In some embodiments, the system will be reset when the current temperature is below the threshold temperature $T_{th}$. In other embodiments, the system will be reset when it reaches a reset temperature $T_{res}$ which is below threshold temperature $T_{th}$. It is also possible that in some embodiments the system does not reset at all, but remains with its mutable system parameters changed until the session is over. Each embodiment may use any or a combination of these reset methods.

The mutable system parameters which can be altered in order to decrease the ultrasonic transducer temperature include, but are not limited to:

Duty Cycle—the system will reduce the amount of time the transmitting piezoelectric elements are active during each transmit-receive cycle.

Applied Voltage—the system decreases the voltage applied to the transmitting elements, which will result in reduced intensity (and temperature).

(Imaging) Mode—the system switches from a higher power imaging mode to a lower power imaging mode, e.g., from harmonic imaging to 2D (fundamental) imaging, from 3D imaging to 2D or harmonic imaging, from 2D mode to M mode, etc.

Frequency—the system decreases the frequency of the ultrasonic sound waves.

Frame Rate—the system decreases the frame rate (number of sweeps per second).

Pulse Repetition Frequency (PRF)—the system decreases the number of beams formed per second.

Aperture—the system decreases the size of the aperture.

(Imaging) Depth—the system decreases the scanning depth.

Sector Width—the system decreases the width of the zone being scanned.

According to other embodiments of the present invention, the manner in which the mutable system parameters change may be rule-based, e.g., it may be desirable for one or more system parameters remain constant while the selected mutable system parameters change (thus requiring the system to alter other, unselected, mutable system parameters). For example, it may be desirable for the F# to stay constant during the session. Thus, if the aperture was selected as the mutable system parameter, the system will also need to alter the depth in order to insure that the F# remains a constant value. Rules may also be much more complex. For instance, a rule may take the form of: <if system parameter X is in state A, change parameter Y by Q amount, but if parameter Z is in state B (as well as X being in A), change parameter W to setting V>. In the preferred embodiments, the system has the rule formats already programmed, e.g., the <if-then> rule format or the <keep this parameter constant by varying those other parameters> rule format is a choice the operator selects, and then the operator fills in the blanks.

As another example of a rule, it may be more desirable to keep a constant image of current color flow than to keep a very accurate image. In this case, a list of mutable system parameters may be used, where the list is in order of decreasing preference. The first mutable system parameter on the list may be applied voltage, or transmit power, while the second mutable system parameter may be frame rate. The system may keep decreasing the transmit power until it reaches a certain limit, e.g., 50% normal transmit power. Then, the system moves on to the second item on the list, frame rate, and begins to decrease that.

Several exemplary embodiments will be discussed below, in order to demonstrate the breadth of the present invention. In the drawings, the same reference numbers are used for similar steps.

Figure 5:
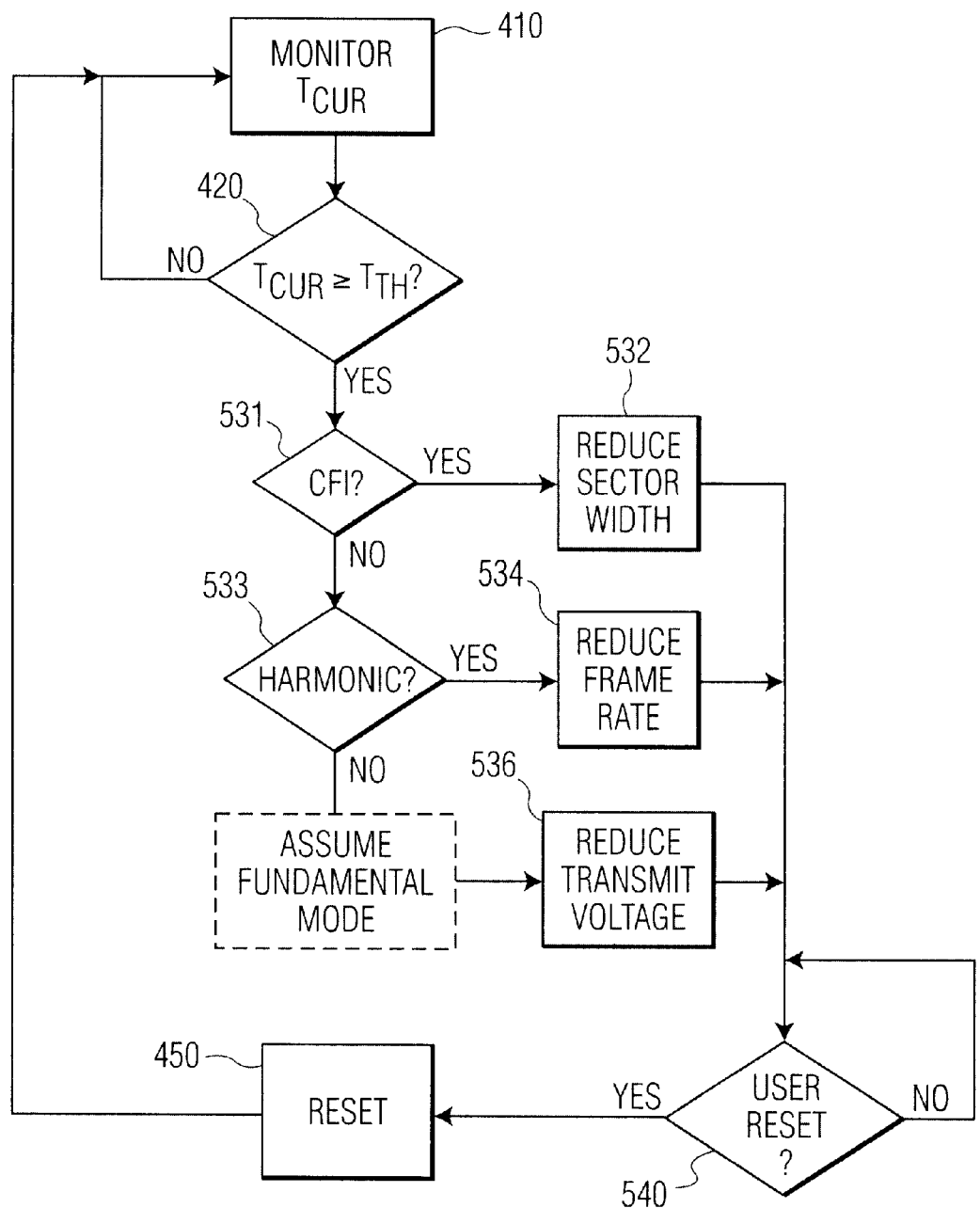
FIG. 5 is a flowchart of a temperature cooling method according to a first exemplary embodiment of the present invention, in which a particular system parameter is changed based on which imaging mode the system is using.

A first exemplary embodiment is shown in FIG. 5. In this embodiment, the mutable system parameter which changes depends on the current imaging mode of the ultrasonic system. Similarly to FIG. 4, the current temperature $T_{cur}$ is monitored in step 410 and, in step 420, it is determined whether the current temperature $T_{cur}$ has exceeded a threshold temperature $T_{th}$. If the current temperature $T_{cur}$ is below the threshold temperature $T_{th}$ in step 420, the system returns to monitoring step 410. If the current temperature $T_{cur}$ is greater than, or equal to, the threshold temperature $T_{th}$ in step 420, the system changes a particular mutable system parameter based on what imaging mode it is in.

Specifically in FIG. 5, the system determines whether it is in color flow imaging mode in step 531. If it is in color flow imaging mode, the sector width is reduced in step 532. If is not in color flow imaging mode, it is determined whether it is in harmonic imaging mode in step 533. If it is, the frame rate is reduced in step 534. If it is not in harmonic imaging mode in step 533, it is assumed that it is in fundamental imaging mode, and the transmit voltage is reduced in step 536. After the mutable system parameter has been changed (in step 532, step 534, or step 536), the user determines whether to reset the system in step 540. If the user decides to reset the system, it is reset in step 450 and returns to monitoring step 410.

In order for the user to determine whether the system should be reset in step 540, the presentation means 350 of the ultrasound system shown in FIG. 3 is an operator's display on which the current status of the ultrasonic transducer is shown. For example, the current temperature of the patient contacting surface or the current rate of heating (or any current system parameter) could be displayed on the monitor. This information can be displayed in a variety of ways: as gauge icons, as digital readouts, as histograms, or any other manner of indicating a quantity on a screen.

Figure 6:
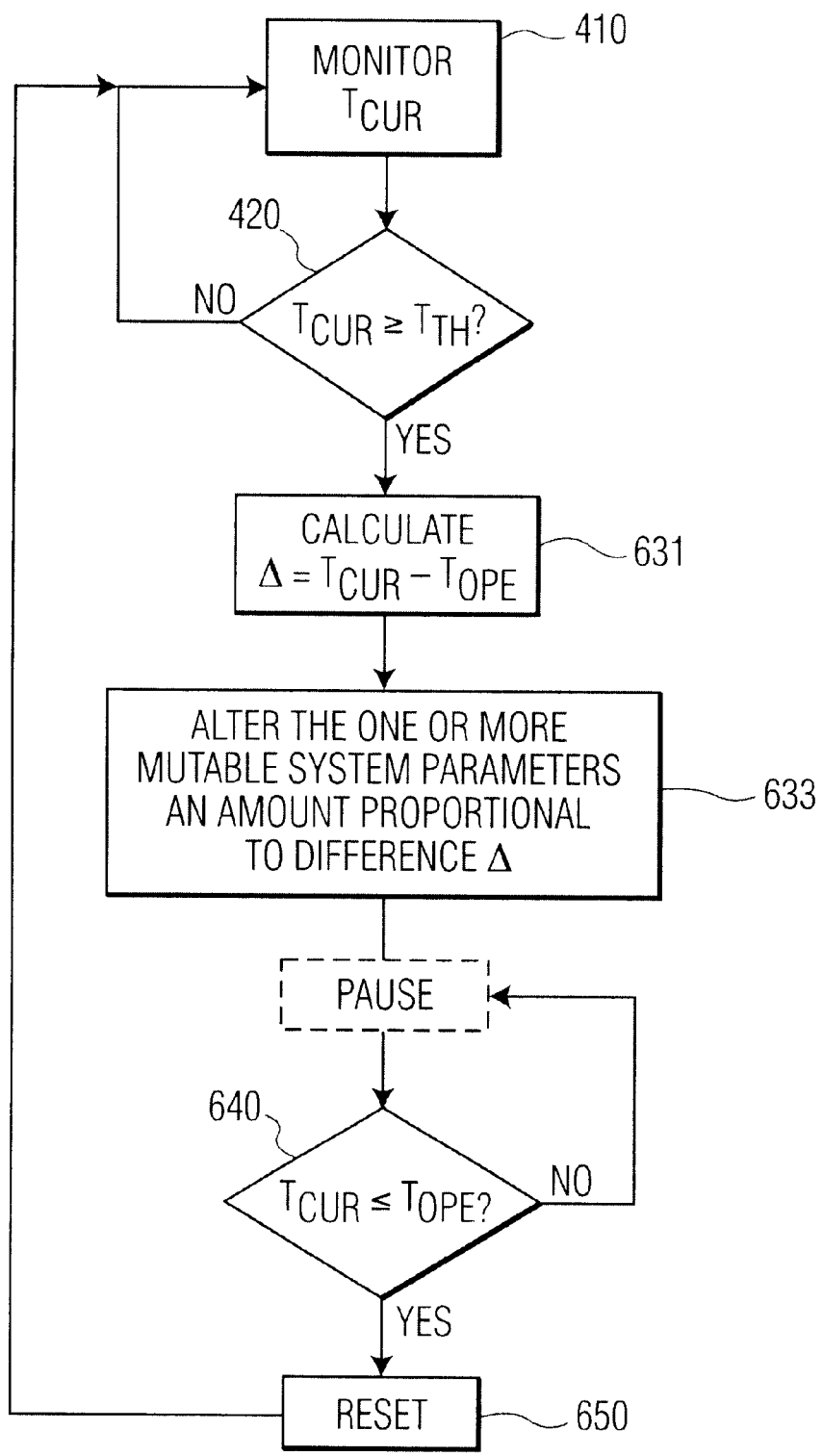
FIG. 6 is a flowchart of a temperature cooling method according to a second exemplary embodiment of the present invention, in which a "semi-closed" feedback loop is used.

A second exemplary embodiment is shown in FIG. 6. In this embodiment, a "semi-closed" loop feedback control is used, in which a feedback loop is used when the threshold temperature $T_{th}$ has been exceeded. Similarly to FIG. 4, the current temperature $T_{cur}$ is monitored in step 410 and, in step 420, it is determined whether the current temperature $T_{cur}$ has exceeded a threshold temperature $T_{th}$. If the threshold temperature $T_{th}$ has been exceeded, the temperature difference $\Delta$ between the current temperature $T_{cur}$ and the preferred operating temperature $T_{ope}$ is determined in step 631. The preferred operating temperature $T_{ope}$ is the optimum temperature for the patient contacting surface of the ultrasonic transducer. In some embodiments, the preferred operating temperature $T_{ope}$ is the same as the threshold temperature $T_{th}$. Next, a predetermined mutable system parameter is changed in proportion to the difference $\Delta$ in step 633. For example, if the predetermined mutable system parameter was the applied voltage (i.e., the voltage applied to the transmitting ultrasonic transducer elements), the applied voltage would be reduced by an amount proportional to the difference $\Delta$. This type of proportionate response provides a very precise adjustment of the system parameter in order to get the intended effect, i.e., reducing the temperature.

After the mutable system parameter has been altered in step 633, it is determined whether the current temperature $T_{cur}$ has become substantially equal to, or less than, the preferred operating temperature $T_{ope}$ in step 640. There may be a deliberate pause between steps 633 and 640 so that the alteration of the mutable system parameter in step 633 has time to cause a decrease in the current temperature $T_{cur}$. If the current temperature is equal to the preferred operating temperature $T_{ope}$ in step 640, the system resets in step 650 and returns to monitoring step 410. If not, the system loops back (with a pause) to determining step 640.

It is possible to eliminate steps 640 and 650, in which case the system returns to monitoring step 410 after reducing the one or more parameters in step 633 (and perhaps after a pause). In other embodiments, the system may return to step 631 if the current temperature $T_{cur}$ has not become substantially equal to, or less than, the preferred operating temperature $T_{ope}$ in step 640. In other words, in such an embodiment, if the current temperature is not equal to the preferred operating temperature $T_{ope}$ in step 640, the system returns to calculating the temperature difference $\Delta$ in step 631 and then alters the mutable system parameter a proportionate amount again in step 633.

Figure 7:
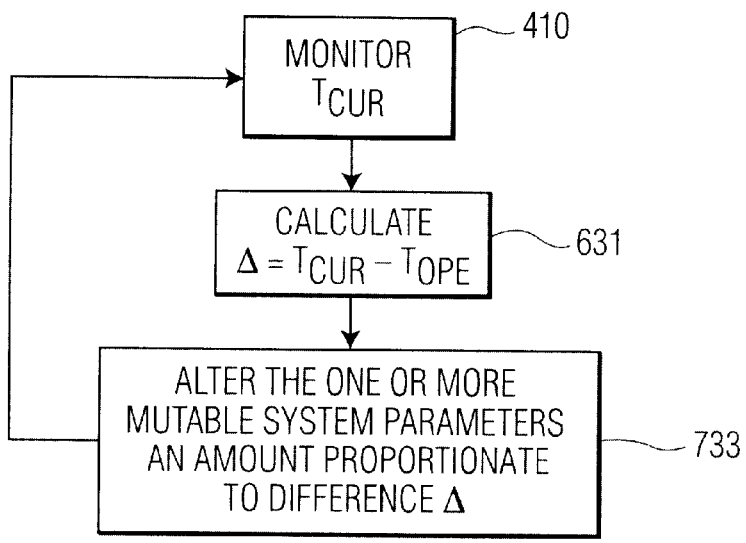
FIG. 7 is a flowchart of a temperature cooling method according to a third exemplary embodiment of the present invention, in which a closed feedback loop is used.

A third exemplary embodiment is shown in FIG. 7. In this embodiment, a "pure" closed loop feedback control is used, in which a feedback loop is continually used to re-adjust one or more system parameters. In FIG. 7, the current temperature $T_{cur}$ is monitored in step 410 and, in step 631, the temperature difference $\Delta$ between the current temperature $T_{cur}$ and the preferred operating temperature $T_{ope}$ is determined. Next, in step 733, one or more mutable system parameters are changed in proportion to the difference $\Delta$. Then, the cycle repeats. There are two essential differences between the semi-closed feedback loop of FIG. 6 and the pure closed feedback loop of FIG. 7. First, the system in step 733 in FIG. 7 may either increase or decrease the mutable system parameter, whereas the system in FIG. 6 may only do one, i.e., increase or decrease the mutable system parameter. For example, if the mutable system parameter was the transmit voltage, step 633 in FIG. 6 would always decrease the transmit voltage, whereas the transmit voltage in step 733 of FIG. 7 would increase or decrease depending on whether the difference $\Delta$ was a negative or positive value. Second, the feedback loop in FIG. 7 is continually looping, whereas the system in FIG. 6 only enters the altering parameters steps if the threshold temperature $T_{th}$ is reached.

Figure 8:
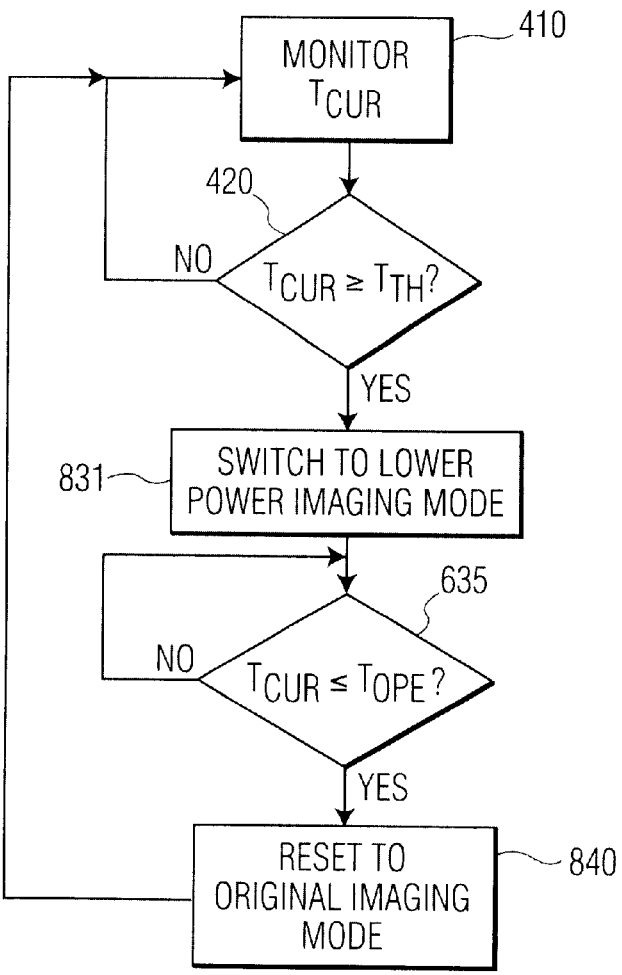
FIG. 8 is a flowchart of a temperature cooling method according to a fourth exemplary embodiment of the present invention, in which the system enters a lower power imaging mode.

A fourth exemplary embodiment is shown in FIG. 8. In this embodiment, the mutable system parameter is the imaging mode, and the overheating prevention method consists of switching from the higher power imaging mode the system is currently in to a lower power imaging mode. In this manner, the overall transmit power (and therefore heating) will be reduced. As in FIGS. 4, 5, and 6, the current temperature $T_{cur}$ is monitored in step 410 and, in step 420, it is determined whether the current temperature $T_{cur}$ has exceeded a threshold temperature $T_{th}$. If the threshold temperature $T_{th}$ has been exceeded, the system goes into a lower power imaging mode in step 831. As an example, if the system was currently in harmonic imaging mode, it would switch to a lower power imaging mode, such as fundamental (2D) imaging.

After the system has entered the lower power imaging mode in step 831, it is determined whether the current temperature $T_{cur}$ has become substantially equal to, or less than, the preferred operating temperature $T_{ope}$ in step 635. If it has not, the system remains in the lower power imaging mode. If the current temperature $T_{cur}$ is substantially equal to, or less than, the preferred operating temperature $T_{ope}$ in step 635, the system is reset in step 840, in which the system returns to whatever imaging mode it was in before entering mixed imaging mode in step 831. Then the system returns to monitoring in step 410. In other embodiments, the user may reset the system to the higher power imaging mode when he or she feels the temperature is sufficiently low.

In other embodiments, the system may perform rapid cycling between a higher power and a lower power imaging mode when the threshold temperature is reached. An example of how this may be done is described in the U.S. patent application Ser. No. 10/268,207 entitled "Imaging Ultrasound Transducer System and Method", filed on Oct. 10, 2002 and assigned to the same assignee. The aforementioned patent application is hereby incorporated by reference.

As stated above, these exemplary embodiments are for illustrative purposes only, and are not intended to limit the present invention in any way. For instance, the steps of any of these exemplary embodiments may be mixed with the steps of any of the other exemplary embodiments. An example of this is shown in FIG. 9, where the steps of the first exemplary embodiment shown in FIG. 5 are combined with a particular example of the general steps of the fourth exemplary embodiment shown in FIG. 8.

Figure 9:
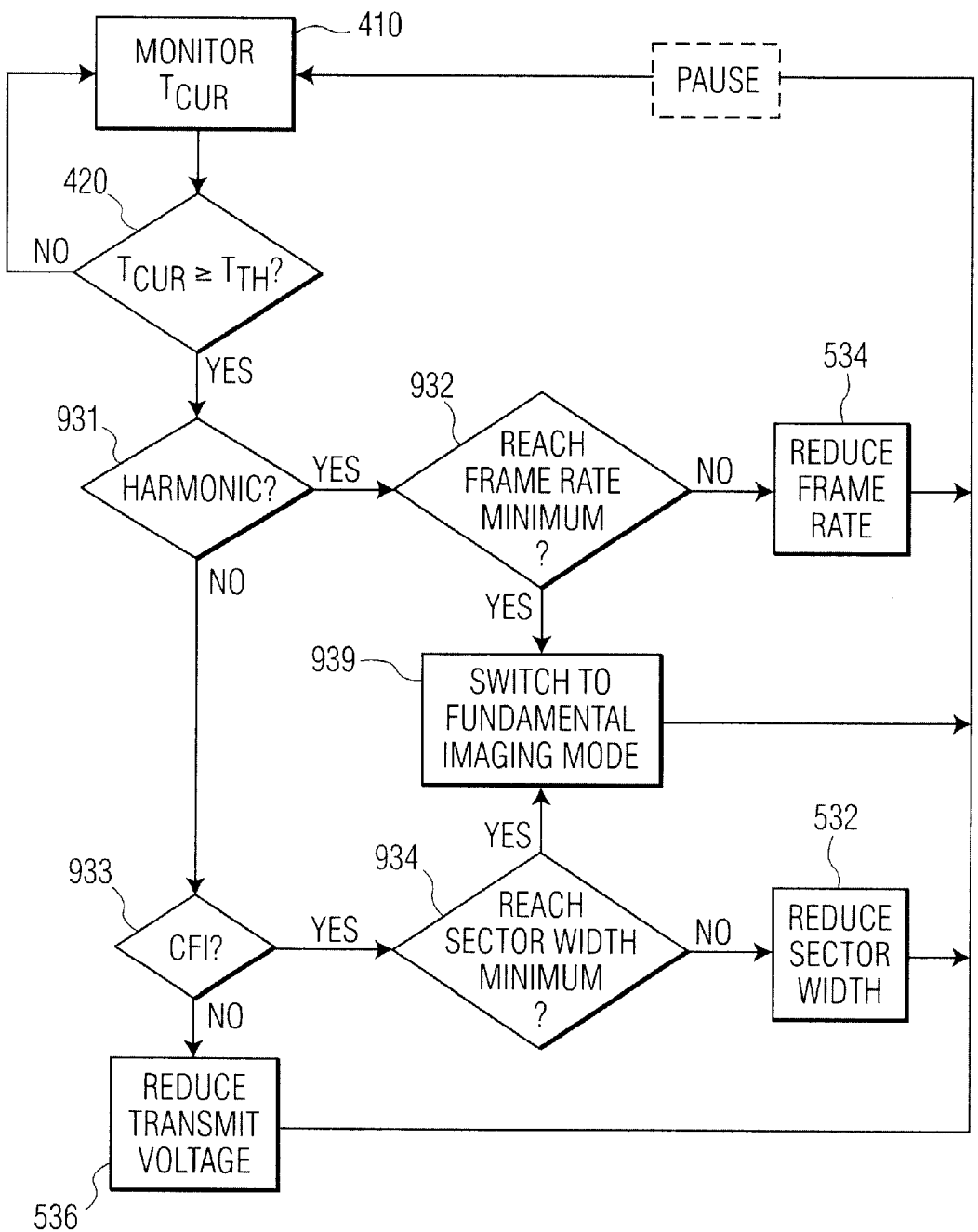
FIG. 9 is a flowchart of a temperature cooling method according to a fifth exemplary embodiment, in which the steps of FIG. 5 are combined with a particular example of the steps of FIG. 8.

In the fifth exemplary embodiment shown in FIG. 9, the system begins by changing one mutable system parameter depending on the current imaging mode of the ultrasonic system, in a manner similar to the first exemplary embodiment of FIG. 5. However, once that mutable system parameter has been reduced to its minimum level of operation, the system changes another system parameter, namely, the imaging mode, in a manner similar to the fourth exemplary embodiment of FIG. 8.

Similarly to the other exemplary embodiments, the system starts by monitoring the current temperature $T_{cur}$ in step 410 and, in step 420, it is determined whether the current temperature $T_{cur}$ has exceeded a threshold temperature $T_{th}$. If the current temperature $T_{cur}$ is below the threshold temperature $T_{th}$ in step 420, the system returns to monitoring step. 410. If the current temperature $T_{cur}$ is greater than, or equal to, the threshold temperature $T_{th}$ in step 420, the system determines whether it is in harmonic imaging mode in step 931. If it is, it is next determined whether the frame rate has been reduced to its minimum in step 932. If it is determined that the frame rate has not been reduced to its minimum in step 932, the frame rate is reduced in step 534. If it is determined that the frame rate has reached its minimum in step 932, the system switches to a lower power imaging mode, namely, the fundamental imaging mode, in step 939.

If it is not in harmonic imaging mode in step 931, it is next determined whether it is in color flow imaging mode in step 933. If it is in color flow imaging mode, it is determined whether the sector width has been reduced to its minimum in step 934. If it is determined that the sector width has not been reduced to its minimum in step 934, the sector width is- reduced in step 532. If it is determined that the sector width has reached its minimum in step 934, the system switches to a lower power imaging mode, namely, the fundamental imaging mode, in step 939. If it is not in color flow imaging mode in step 933, the transmit voltage is reduced in step 536. The steps of determining which imaging mode the system is in (steps 931 and 933) are in reverse order from FIG. 5 in order to show that these steps are abstract and conceptual, and they may occur in any order and at any time.

After one of the mutable system parameters has been changed (in step 532, step 534, step 536, or step 939), the system pauses for a moment (for the parameter change to cause a decrease in temperature) and then returns to monitoring step 410. In this embodiment, the system is not reset, but continues to reduce the particular system parameter (if in harmonic or color flow imaging mode) until it reaches a minimum, at which time it changes imaging mode. The other embodiments could operate in this manner (with no reset), and this embodiment may have additional steps added, where the system or the operator may reset the changed parameter once the temperature is below a certain threshold.

Likewise, there are many additional steps which are compatible with the embodiments of the present invention, some of which are described below.

In some embodiments, the operator selects the mutable system parameter(s) as well as the type and amount of change. In one such embodiment, the ultrasonic system warns the operator that the temperature is dangerously close to excessive during the session and prompts the operator to choose one or more mutable system parameters to change in order to reduce the temperature on the patient contacting surface. In another such embodiment, the user monitors the temperature and other parameters of the ultrasonic system and interacts directly with the system in order to alter the one or more system parameters before the temperature reaches a critical point. The operator may do this at any point during the ultrasonic session. In yet another such embodiment, the user selects beforehand the mutable system parameters that will be altered automatically during the session. Examples of user-supervised transducer cooling systems are described in the U.S. patent application Ser. No. 10/269,144 entitled "Operator Supervised Temperature Control System and Method for an Ultrasound Transducer", filed on Oct. 11, 2002 and assigned to the same assignee. The aforementioned patent application is hereby incorporated by reference.

In other embodiments, there are additional steps to prevent the ultrasonic transducer from reaching a critical temperature where the patient may be hurt or made uncomfortable. In those embodiments, the ultrasonic transducer turns off when the temperature reaches the critical point.

While there have shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method of cooling an imaging ultrasonic transducer in an ultrasonic transducer system comprising the steps of:

determining a temperature of the imaging ultrasonic transducer; and implementing a change in at least one mutable system parameter of the imaging ultrasonic transducer based on the determined temperature of the imaging ultrasonic transducer, wherein the change implemented is determined according to a current imaging mode of the ultrasonic transducer system.

2. The method of claim 1, wherein the step of implementing a change in at least one mutable system parameter based on the determined temperature of the imaging ultrasonic transducer comprises the steps of:

determining if the determined temperature is greater than, or equal to, a threshold temperature; and implementing, if it is determined that the determined temperature is greater than, or equal to, a threshold temperature, the change in the at least one mutable system parameter.

3. The method of claim 2, wherein the step of implementing, if it is determined that the determined temperature is greater than, or equal to, a threshold temperature, the change in at least one mutable system parameter comprises the steps of:

if the current imaging mode is a fundamental mode, reducing an applied voltage to transmitting elements in the ultrasonic transducer;

if the current imaging mode is a harmonic mode, reducing a frame rate of the ultrasonic transducer; and if the current imaging mode is a color flow imaging mode, reducing a color sector width.

4. The method of claim 3, wherein the step of implementing, if it is determined that the determined temperature is greater than, or equal to, a threshold temperature, the change in at least one mutable system parameter further comprises the steps of:

before the step of reducing the color sector width, determining if the color sector width is at a minimum level, changing to the fundamental imaging mode if the color sector width is at a minimum level; and before the step of reducing the frame rate, determining if the frame rate is at a minimum level, changing to the fundamental imaging mode if the frame rate is at a minimum level.

5. The method of claim 1, wherein the step of implementing a change in at least one mutable system parameter based on the determined temperature is comprised of the step of:

using a closed loop feedback control algorithm to adjust the at least one mutable system parameter, wherein the feedback is the determined temperature.

6. The method of claim 5, wherein the closed loop feedback control algorithm is one of linear and nonlinear.

7. The method of claim 1, wherein the step of implementing a change in at least one mutable system parameter based on the determined temperature is comprised of the step of:

changing the at least one system parameter, wherein an amount of change in the at least one mutable system parameter is based on an amount of temperature variation from a predetermined operating temperature value.

8. The method of claim 7, wherein the step of changing the at least one system parameter uses a proportional-integral-derivative (PID) algorithm to determine the amount of change in the at least one mutable system parameter based on the amount of temperature variation from the predetermined operating temperature value.

9. The method of claim 1, wherein a basis of the change is at least one of:

an amount the determined temperature is above or below a predetermined temperature value; or whether the determined temperature is equal to or greater than a predetermined threshold temperature value.

10. The method of claim 1, wherein the ultrasonic transducer system is in a non-fundamental imaging mode, and wherein the change is:
    changing the imaging mode to fundamental imaging mode if the determined temperature is about 42 degrees or above.

11. The method as recited in claim 1, wherein the at least one mutable system parameter comprises at least one of:
    duty cycle, wherein the duty cycle is the amount of time in which the ultrasonic transducer is transmitting during each transmit-receive cycle;
    applied voltage to transmitting elements in the ultrasonic transducer;
    frequency of the ultrasonic sound waves;
    frame rate of the ultrasonic transducer;
    pulse repetition frequency (PRF) of the ultrasonic transducer;
    aperture of the ultrasonic transducer;
    imaging depth of the ultrasonic transducer;
    sector width of the ultrasonic transducer; and
    imaging mode of the ultrasonic transducer.

12. The method of claim 1, wherein the step of implementing a change in at least one mutable system parameter based on the determined temperature is comprised of the step of:
    switching from a desired higher power imaging mode to a less desired lower power imaging mode.

13. The method of claim 1, further comprising the step of:
    resetting the at least one mutable system parameter back to an original state, said original state being a state of the at least one mutable system parameter before the change was implemented.

14. The method of claim 13, wherein the resetting step is at least one of: a) initiated by an operator of the ultrasonic transducer system, b) initiated by the ultrasonic transducer system when the ultrasonic transducer has cooled sufficiently, and c) initiated by the ultrasonic transducer system after a prescribed period of time.

15. The method of claim 1, further comprising the steps of:
    determining whether the determined temperature of the ultrasonic transducer is greater than or equal to a critical temperature;
    turning the ultrasonic transducer off if it is determined that the determined temperature is greater than or equal to the critical temperature; and
    once the ultrasonic transducer has been turned off:
        determining a current temperature of the ultrasonic transducer;
        determining whether the current temperature is less than the critical temperature; and
        turning the ultrasonic transducer back on if it is determined that the current temperature is less than the critical temperature.

16. A system for cooling an ultrasonic transducer in an ultrasonic transducer system, comprising:
    at least one temperature sensor for sensing the temperature of at least a portion of the ultrasonic transducer; and
    a controller for implementing a change in at least one mutable system parameter depending on the temperature sensed by the at least one temperature sensor, wherein the change will cause a reduction in the temperature of the ultrasonic transducer, and wherein the change implemented by the controller is determined according to a current imaging mode of the ultrasonic transducer system.

17. The system of claim 16, wherein the controller determines if the sensed temperature is greater than, or equal to, a threshold temperature and implements, if it is determined that the determined temperature is greater than, or equal to, a threshold temperature, the appropriate change in at least one mutable system parameter.

18. The system of claim 16, wherein the controller uses a closed loop feedback control algorithm to adjust the at least one mutable system parameter.

19. The system of claim 16, wherein the controller changes the at least one system parameter, wherein an amount of change in the at least one mutable system parameter is based on an amount of temperature variation from a predetermined operating temperature value.

20. The system as recited in claim 16, wherein the at least one mutable system parameter comprises at least one of:
    duty cycle, wherein the duty cycle is the amount of time in which the ultrasonic transducer is transmitting during each transmit-receive cycle;
    applied voltage to transmitting elements in the ultrasonic transducer;
    frequency of the ultrasonic sound waves;
    frame rate of the ultrasonic transducer;
    pulse repetition frequency (PRF) of the ultrasonic transducer;
    aperture of the ultrasonic transducer;
    imaging depth of the ultrasonic transducer;
    sector width of the ultrasonic transducer; and
    imaging mode of the ultrasonic transducer.

21. The system of claim 16, wherein:
    if the current imaging mode is a fundamental mode, reducing an applied voltage to transmitting elements in the ultrasonic transducer;
    if the current imaging mode is a harmonic mode, reducing a frame rate of the ultrasonic transducer; and
    if the current imaging mode is a color flow imaging mode, reducing a color sector width.

* * * * *